United States Patent
Bohrisch et al.

(10) Patent No.: US 7,508,905 B2
(45) Date of Patent: Mar. 24, 2009

(54) HEATING DEVICE IN MAMMOGRAPHY SYSTEMS

(75) Inventors: Silvia Bohrisch, Mountain View, CA (US); Wolfgang Holler, Erlangen (DE); Martin Ramsauer, Pyrbaum (DE)

(73) Assignee: Siemens Aktiengesellschaft (DE)

( * ) Notice: Subject to any disclaimer, the term of this patent is extended or adjusted under 35 U.S.C. 154(b) by 20 days.

(21) Appl. No.: 11/661,897

(22) PCT Filed: Sep. 6, 2005

(86) PCT No.: PCT/EP2005/054391

§ 371 (c)(1),
(2), (4) Date: Mar. 1, 2007

(87) PCT Pub. No.: WO2006/027358

PCT Pub. Date: Mar. 16, 2006

(65) Prior Publication Data

US 2008/0107232 A1    May 8, 2008

(30) Foreign Application Priority Data

Sep. 8, 2004    (DE) .................. 10 2004 043 532

(51) Int. Cl.
*A61B 6/04* (2006.01)
(52) U.S. Cl. .................................................... 378/37
(58) Field of Classification Search ................ 378/37
See application file for complete search history.

(56) References Cited

U.S. PATENT DOCUMENTS

| 5,081,657 A | 1/1992 | Klawitter et al. |
| 6,120,529 A | 9/2000 | Hartge et al. |
| 2008/0253512 A1* | 10/2008 | Fischer et al. .............. 378/37 |

FOREIGN PATENT DOCUMENTS

| DE | 195 33 753 C1 | 11/1996 |
| DE | 200 09 838 U1 | 8/2000 |
| EP | 0 152 592 A1 | 8/1985 |
| EP | 0 796 637 A2 | 9/1997 |
| GB | 1 490 381 | 11/1977 |
| GB | 2 350 125 A | 4/1997 |

* cited by examiner

*Primary Examiner*—Allen C. Ho
(74) *Attorney, Agent, or Firm*—Brinks Hofer Gilson & Lione

(57) ABSTRACT

A mammography unit is provided. The mammography unit includes a stand; an X-ray unit; a compression unit that includes a compression plate; an object table; and a suspension of the X-ray and compression units or the object table. The suspension is height-adjustable relative to the stand. The compression plate and the object table are adjustable relative to one another. At least one radiation element is integrated into the mammography unit. The at least one radiation element is operable to heat the object table by exposure to radiation.

15 Claims, 3 Drawing Sheets

PRIOR ART

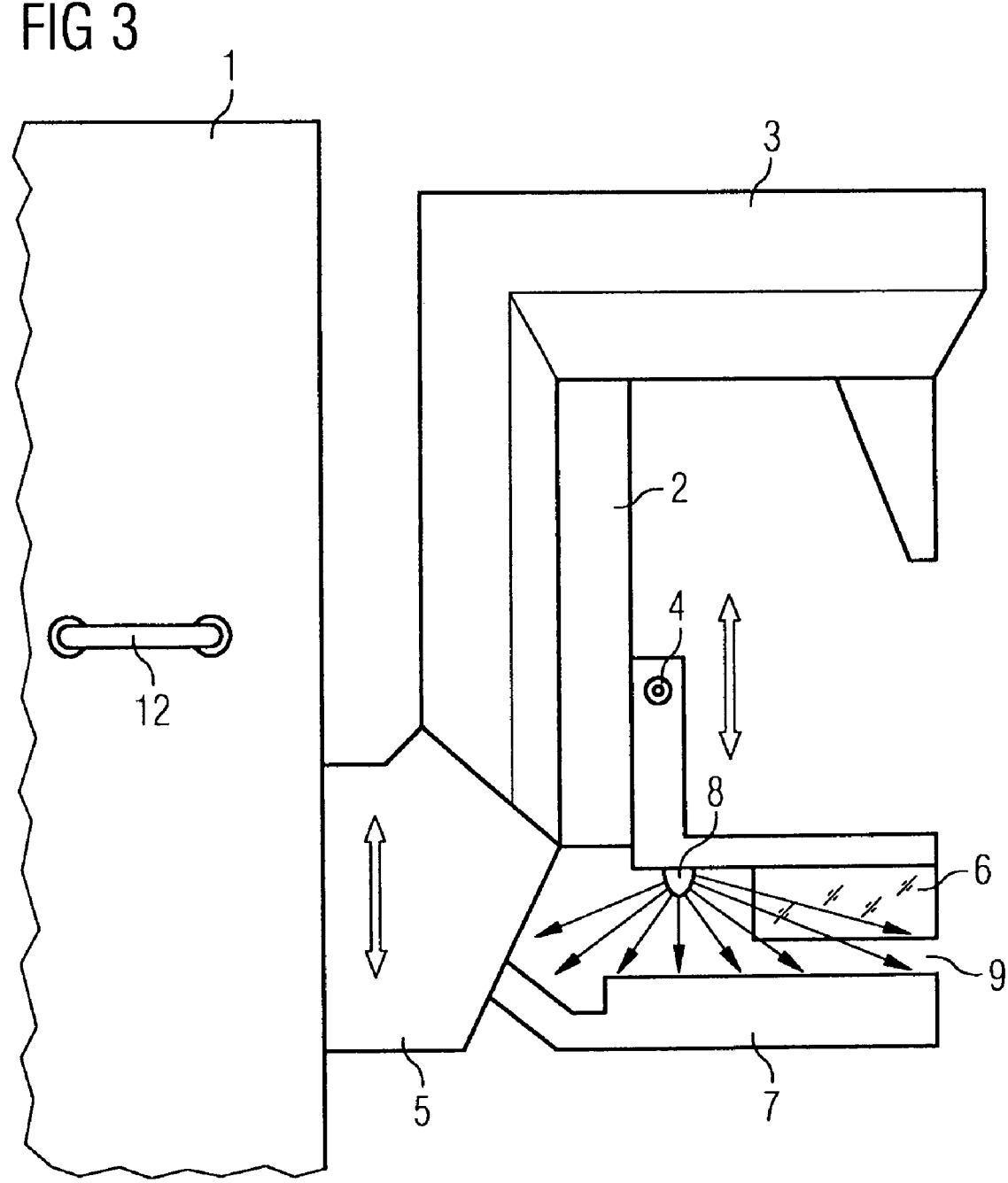

HEATING DEVICE IN MAMMOGRAPHY SYSTEMS

The present patent document is a §371 nationalization of PCT Application Serial Number PCT/EP2005/054391, filed Sep. 6, 2005, designating the United States, which is hereby incorporated by reference. This patent document also claims the benefit of DE 10 2004 043 532.4, filed Sep. 8, 2004, which is also hereby incorporated by reference.

BACKGROUND

The present embodiments relate to a heating device in mammography systems.

Mammography is X-ray based medical imaging technology for examining the female breast for abnormal changes in tissue. Mammography can be used to detect life-threatening (scattered) tumors in their early stages so that they can be surgically removed.

Mammography is used successfully in the field of cancer screening for women. Mammography is increasing in popularity because of a growing awareness of public health.

In a conventional standard mammography examination, the breast to be examined is placed on an object table which is located at breast height of the standing or sitting patient. The object table comprises the X-ray film to be exposed together with other technical components (screens, films, detectors, filters etc.). The breast is then gently squeezed horizontally using a height-adjustable, preferably transparent compression plate. The breast is exposed several times from different angles, sometimes using stereotactic recordings, by briefly switching on the X-ray source. After the image recording process and/or a subsequent biopsy (removal of tissue using a hollow needle) the breast may be released again.

One known problem in mammography is the relatively high thermal conductivity of the compression plate and the object table. The high thermal conductivity causes the patient to experience an unpleasantly cold feeling upon initial contact with the breast.

Until now electric blankets or heating pads or films have been laid on the object table (also referred to as a "Bucky table"). In order to establish good thermal contact, these heating elements have been attached using rubber bands, wires or the like which is an extremely laborious procedure. In conventional mammography units, there is no separate storage option provided for these heating elements. The heating elements are stored anywhere and are exposed to natural soiling.

Because the heating elements are stored anywhere and are exposed to natural soiling, the use of such heating elements is in many cases dispensed with by operating staff of a mammography unit, which is to the detriment of the patients.

US patent specification U.S. Pat. No. 5,081,657 discloses a heating element, which facilitates its implementation and enables improved storage in terms of hygiene. As shown in FIG. 1, the heating element 13 according to U.S. Pat. No. 5,081,657 includes a two-walled shell 10, which is a J-shaped section, and is made of a good heat conducting material. The heating element 13 is heated from within by an electrically operated heating film 11. The electrical supply 13 is integrated within the suspension 5 of the stand 1. The J-shaped section is adapted to the thickness of the object table 7. The shell 10 can be fitted over the object table 7 immediately before the examination. The fit enables good thermal contact. The heat of the shell passes to the object table 7 via the thermal contact. When the heating element 13 is not in use, the heating element 13 can be attached to a suspension 12 fixed to a stand 1 and stored until the next use.

Nonetheless such a heating element is complex and an error-prone component. The heating element is expensive to manufacture and is a cost-intensive component. Even a suspension does not guarantee hygienic, perfect storage over a long period of time.

SUMMARY

The present embodiments may obviate one or more of the drawbacks or limitations inherent in the related art. For example, in one embodiment, a mammography unit enables technically simple, cost-effective and, from the hygiene point of view, optimal heating of the surfaces in contact with the patient.

A mammography unit includes a stand, an X-ray unit, a compression unit, an object table, and a suspension of the X-ray and compression units or the object table. The Object table is height-adjustable relative to the stand. A compression plate is associated with the compression unit. The compression plate and the object table are adjustable relative to one another with at least one X-ray element being integrated in the mammography unit such that ht object table is heated by radiation from the radiation element.

In one embodiment, the radiation element is integrated into the device in such a way that it also heats the compression plate at the same time.

The at least one radiation element can be attached to the suspension of the X-ray and compression unit or the object table. Alternatively, the at least one radiation element can be attached to the lower surface of the compression unit.

The mammography unit may include two radiation elements. One radiation element is attached to the suspension of the X-ray and compression unit or the object table. The other radiation element is attached to the lower surface of the compression unit.

The radiation element may be an infrared lamp or an infrared emitter.

BRIEF DESCRIPTION OF THE FIGURES

FIG. 3 illustrates one embodiment of a mammography unit with a first and a second heating device.

DETAILED DESCRIPTION

Figure 1:
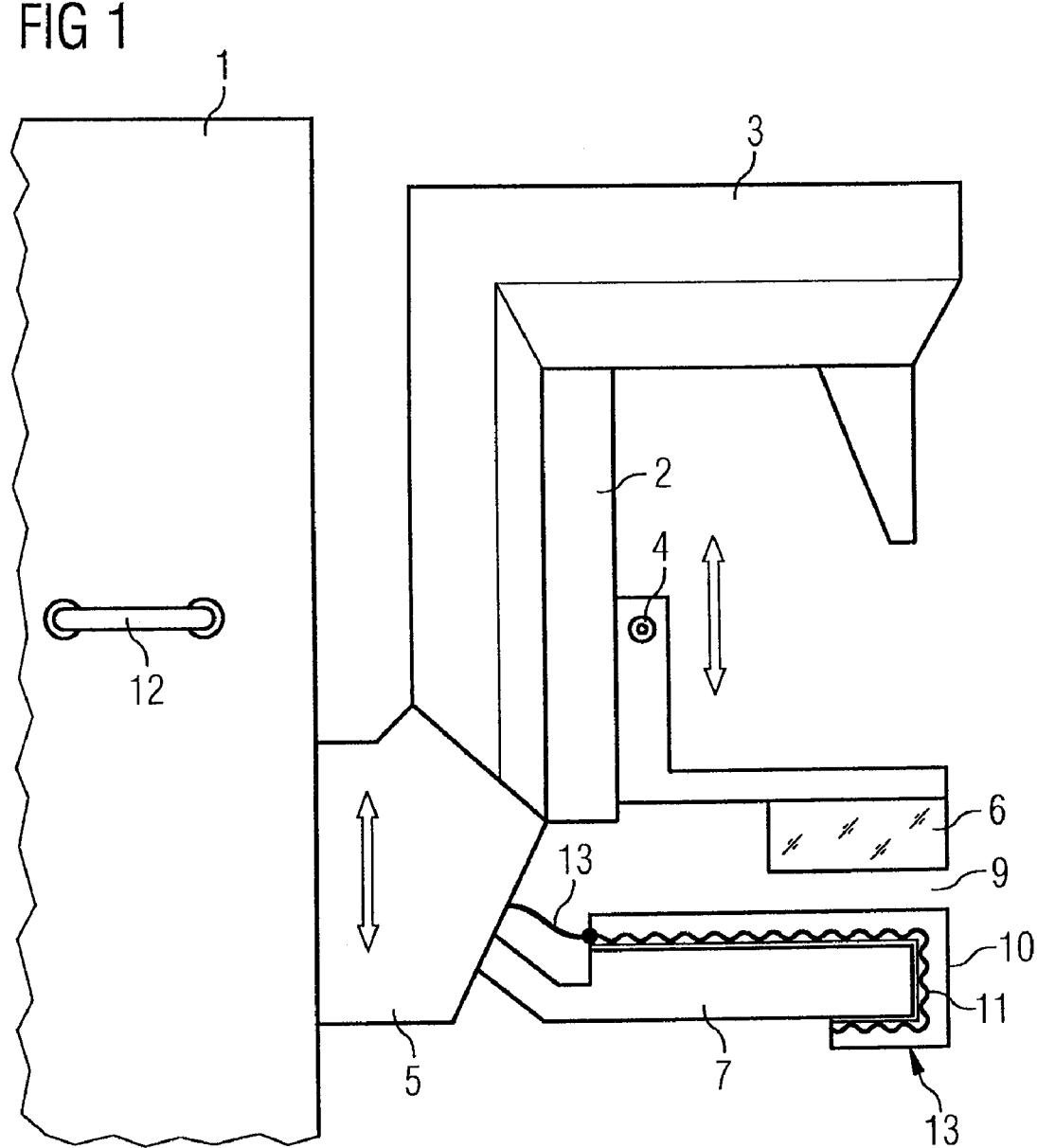
FIG. 1 illustrates a mammography unit with a heating element for heating the object table according to the prior art.
Figure 2:
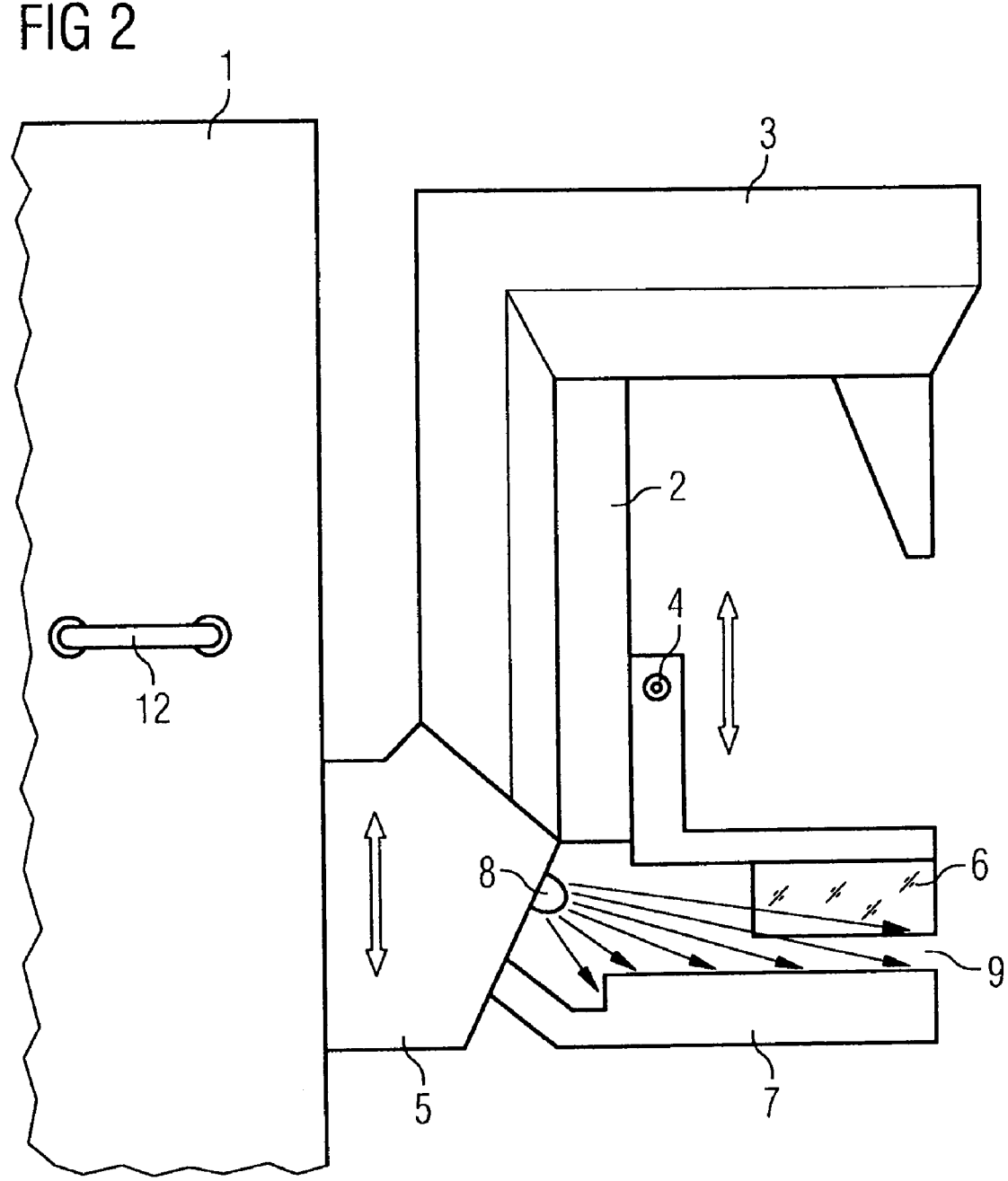
FIG. 2 illustrates one embodiment of a mammography unit with a first heating device.

In one embodiment, as shown in FIG. 2, a mammography unit includes a stand 1 with a height-adjustable suspension 5 attached to it. The height-adjustable nature is indicated by a bidirectional vertical arrow. The suspension 5 supports the X-ray unit 3 and the object table 7. The object table 7 can be adjusted to the individual breast height of the patients because of the height-adjustable nature of the suspension 5.

The object table 7 comprises the X-ray film that is exposed during brief activation of the X-ray emitter 3. The X-ray beam cone penetrates the breast lying on the object table 7 and creates a breast tissue-dependent absorption image. The object table 7 may include additional technical components not described in more detail.

The breast is distributed as evenly as possible on a surface of the object table 7, which is as large as possible, to produce a higher resolution image and allow for better diagnosis. A compression unit 2 is attached to the X-ray unit 3. A compression plate 6 can be vertically adjusted by using a knob 4. The breast can be distributed via a compression unit 2 by slight pressure on the object table 7 in a flat horizontal gap 9.

The compression plate 6 only serves for the shaping of the breast. The compression plate 6 should not appear in the X-ray image. The compression plate 6 is made from transparent material (such as acrylic plastic).

Both the object table 7 and the compression plate 6 are normally at room temperature but have a high thermal conductivity. The patient experiences an unpleasant subjective feeling of cold when the object table 7 and the compression plate 6 come into contact with the breast because of the height thermal conductivity.

The object table 7 and the lower surface of the compression plate 6 is pre-heated by exposure to radiation with infrared light to a temperature that the patient finds pleasant when in contact with the breast.

In one embodiment, as shown in FIG. 2, an infrared emitter or an infrared lamp 8 is attached to a suspension 5 in such a way that the thermal radiation entirely encompasses the lower surface of the compression plate 6 and the upper surface of the object table 7.

In one embodiment, as shown in FIG. 3, the infrared heat emitter 8 is alternatively or additionally fastened to the lower surface of the vertically adjustable element of the compression unit 2.

The thermal radiation emitted by the IR emitter 8, as shown by arrows in FIGS. 2 and 3, reaches the surfaces that need heating (lower surface of the compression plate 5 and upper surface of the object table 7). An electrical switch for turning the IR emitter(s) on and off can be mounted at any location (e.g. on the stand 1).

Indirect and non-contact heating increases the patient's comfort during a mammographic examination since the compression plate is also heated at the same time.

Indirect and non-contact heating improves operator's comfort, when compared to a solution with heating wires or elements. The IR emitter only has to be turned on and off and replaced when necessary.

Indirect and non-contact heating decreases the risk of hygiene problems since non-contact heating foregoes the need to clean a heating element or store it carefully.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A mammography unit comprising:
 a stand;
 an X-ray unit;
 a compression unit that includes a compression plate;
 an object table, the compression plate and the object table being adjustable relative to one another; and,
 a suspension of the X-ray and compression units or the object table, the suspension being height-adjustable relative to the stand,
 wherein at least one radiation element is fixed to the suspension and is operable to heat the object table by exposure to radiation.

2. The mammography unit as claimed in claim 1, wherein the at least one radiation element is operable to heat the compression plate.

3. The mammography unit as claimed in claim 2, wherein the at least one radiation element is operable to simultaneously heat the compression plate and the object table.

4. The mammography unit as claimed in claim 1, wherein the at least one radiation element includes an infrared lamp.

5. The mammography unit as claimed in claim 1, wherein the at least one radiation element includes an infrared emitter.

6. A mammography unit comprising:
 a stand;
 an X-ray unit;
 a compression unit that includes a compression plate;
 an object table, the compression plate and the object table being adjustable relative to one another; and,
 a suspension of the X-ray and compression units or the object table, the suspension being height-adjustable relative to the stand,
 wherein at least one radiation element is integrated into the compression unit and is operable to heat the object table by exposure to radiation, the at least one radiation element being attached to a lower surface of the compression unit.

7. The mammography unit as claimed in claim 6, wherein the at least one radiation element is operable to heat the compression plate.

8. The mammography unit as claimed in claim 7, wherein the at least one radiation element is operable to simultaneously heat the compression plate and the object table.

9. The mammography unit as claimed in claim 6, wherein the at least one radiation element includes an infrared lamp.

10. The mammography unit as claimed in claim 6, wherein the at least one radiation element includes an infrared emitter.

11. A mammography unit comprising:
 a stand;
 an X-ray unit;
 a compression unit that includes a compression plate;
 an object table, the compression plate and the object table being adjustable relative to one another; and
 a suspension of the X-ray and compression units or the object table, the suspension being height-adjustable relative to the stand,
 wherein a first radiation element and a second radiation element are operable to heat the object table by exposure to radiation, and
 wherein the first radiation element is attached to the suspension and the second radiation element is attached to a lower surface of the compression unit.

12. The mammography unit as claimed in claim 11, wherein the first and second radiation elements are operable to heat the compression plate.

13. The mammography unit as claimed in claim 12, wherein the first and second radiation elements are operable to simultaneously heat the compression plate and the object table.

14. The mammography unit as claimed in claim 11, wherein at least one of the first and second radiation elements includes an infrared lamp.

15. The mammography unit as claimed in claim 11, wherein at least one of the first and second radiation elements includes an infrared emitter.

* * * * *